United States Patent
Samaniego et al.

(10) Patent No.: US 10,279,081 B2
(45) Date of Patent: May 7, 2019

(54) COMPOSITE GRAFTS, SYSTEMS, AND METHODS

(71) Applicant: AlloSource, Centennial, CO (US)

(72) Inventors: Adrian C. Samaniego, Highlands Ranch, CO (US); Matthew Southard, Denver, CO (US); Kenneth Blood, Littleton, CO (US)

(73) Assignee: ALLOSOURCE, Centennial, CO (US)

( * ) Notice: Subject to any disclaimer, the term of this patent is extended or adjusted under 35 U.S.C. 154(b) by 498 days.

(21) Appl. No.: 14/923,087

(22) Filed: Oct. 26, 2015

(65) Prior Publication Data

US 2016/0114079 A1 Apr. 28, 2016

Related U.S. Application Data

(60) Provisional application No. 62/068,299, filed on Oct. 24, 2014.

(51) Int. Cl.
*A61L 27/56* (2006.01)
*A61L 27/54* (2006.01)
*A61L 27/36* (2006.01)
*A61L 27/38* (2006.01)
*A61F 2/28* (2006.01)

(52) U.S. Cl.
CPC .......... *A61L 27/54* (2013.01); *A61L 27/3604* (2013.01); *A61L 27/3834* (2013.01); *A61F 2002/2835* (2013.01); *A61L 2300/414* (2013.01); *A61L 2300/64* (2013.01)

(58) Field of Classification Search
None
See application file for complete search history.

(56) References Cited

U.S. PATENT DOCUMENTS

| | | | | |
|---|---|---|---|---|
| 5,711,960 A | * | 1/1998 | Shikinanni | A61F 2/0063 424/425 |
| 5,885,829 A | * | 3/1999 | Mooney | A61L 27/3604 424/422 |
| 7,419,482 B2 | * | 9/2008 | Nash | A61B 17/32037 128/898 |
| 7,866,878 B2 | | 1/2011 | Howe et al. | |
| 8,071,007 B1 | | 12/2011 | Teoh et al. | |
| 8,182,532 B2 | | 5/2012 | Anderson et al. | |
| 2002/0182241 A1 | * | 12/2002 | Borenstein | A61F 2/0077 424/422 |
| 2004/0078090 A1 | * | 4/2004 | Binette | A61L 27/36 623/23.76 |
| 2005/0125077 A1 | * | 6/2005 | Harmon | A61L 27/3683 623/23.72 |
| 2006/0195188 A1 | | 8/2006 | O'Driscoll et al. | |
| 2007/0065652 A1 | | 3/2007 | Liebschner | |
| 2007/0191963 A1 | * | 8/2007 | Winterbottom | A61F 2/28 623/23.5 |
| 2007/0255422 A1 | | 11/2007 | Wei et al. | |
| 2008/0081362 A1 | * | 4/2008 | Keeley | A61L 27/3604 435/283.1 |
| 2009/0092674 A1 | * | 4/2009 | Ingram | A61K 31/715 424/499 |
| 2009/0130175 A1 | | 5/2009 | Liebschner et al. | |
| 2009/0216252 A1 | * | 8/2009 | Melvin | A61B 17/0057 606/151 |
| 2010/0254212 A1 | | 10/2010 | Howe et al. | |
| 2012/0121793 A1 | * | 5/2012 | Chang | A61L 15/325 427/2.31 |
| 2014/0236299 A1 | | 8/2014 | Roeder et al. | |
| 2014/0271570 A1 | | 9/2014 | Shi et al. | |
| 2015/0119994 A1 | | 4/2015 | Kang et al. | |
| 2015/0366655 A1 | | 12/2015 | Tumey et al. | |

FOREIGN PATENT DOCUMENTS

| | | |
|---|---|---|
| WO | 2000040177 | 7/2000 |
| WO | 2014037713 A1 | 3/2014 |

OTHER PUBLICATIONS

Dumas, J. E., et al., "Synthesis, characterization, and remodeling of weight-bearing allograft bone/polyurethane composites in the rabbit", Acta Biomaterialia vol. 6, pp. 2394-9406 (2010); epub: Jan. 28, 2010.

Shikinami, Y., et al. "The complete process of bioresorption and bone replacement using devices made of forged composites of raw hydroxyapatite particles/poly I-lactide (F-u-HA/PLLA)", Biomaterials vol. 26(27), pp. 5542-5551, Sep. 2005.

* cited by examiner

*Primary Examiner* — Julie Wu
*Assistant Examiner* — Douglas F White
(74) *Attorney, Agent, or Firm* — Kilpatrick Townsend & Stockton LLP

(57) ABSTRACT

Composite grafts including a biocompatible, synthetic scaffold; and a biological tissue component obtained or derived from a deceased donor tissue, wherein the biological tissue component is embedded in the biocompatible, synthetic scaffold, are provided as systems relating thereto. Methods of manufacture and methods of treatment using such grafts are also provided.

17 Claims, 13 Drawing Sheets

COMPOSITE GRAFTS, SYSTEMS, AND METHODS

CROSS-REFERENCE TO RELATED APPLICATION

This application claims the benefit under 35 U.S.C. § 119 (e) of U.S. Provisional Patent Application No. 62/068,299, filed Oct. 24, 2014, which is hereby incorporated herein by reference in its entirety.

BACKGROUND

Human tissue compositions, which may be derived from deceased donors, have been used for many years in various surgical procedures, including treatments for certain medical conditions, including tissue defects and wounds and in reconstructive surgical procedures.

Medical grafting procedures often involve the implantation of autografts, allografts, or synthetic grafts into a patient to treat a particular condition or disease. An autograft is tissue obtained from another location in the recipient's body, while an allograft is tissue obtained from an individual (donor) other than the recipient. Allograft tissue is often taken from deceased donors that have donated their tissue for medical uses to treat living people. Such tissues represent a gift from the donor or the donor family to enhance the quality of life for other people.

The use of musculoskeletal allograft tissue in reconstructive orthopedic procedures and other medical procedures has markedly increased in recent years, and millions of musculoskeletal allografts have been safely transplanted. A common allograft is bone. One example of this is bone allografts used to treat patients whose bones have degenerated from cancer. Typically, bone grafts are reabsorbed and replaced with the patient's natural bone upon healing. Bone grafts can be used in a variety of indications, including neurosurgical and orthopedic spine procedures for example. In some instances, bone grafts can be used to fuse joints or to repair broken bones. In some cases, bone material is combined with mesenchymal stem cells to produce a graft composite.

Tissue grafts may also have reconstructive applications. For example, currently reconstructive techniques to fill a lumpectomy often use either the patient's own fat from a secondary surgical site (autograft) or foreign implantable material (synthetic graft). However, both types of procedures have limitations. In an allograft procedure, healing of the secondary surgical site may result in a depression or divot, while synthetic grafts may be rejected or encapsulated.

Tissue grafts are often implemented in various industries related to orthopedics, reconstructive surgery, podiatry, and cartilage replacement. In some cases, currently known tissue grafts offer limited manipulability in adjusting tissue uniformity, flexibility, and/or porosity.

Hence, although presently used reconstructive surgical techniques and tissue graft compositions and methods provide real benefits to patients in need thereof, still further improvements are desirable. The present disclosure provides solutions to at least some of these outstanding needs.

BRIEF SUMMARY

Provided are composite grafts, systems, and methods relating thereto.

In one aspect, a composite includes a biocompatible, synthetic scaffold; and a biological tissue component obtained or derived from a deceased donor tissue, wherein the biological tissue component is embedded in the biocompatible, synthetic scaffold. The biocompatible, synthetic scaffold may be a polymerized silicone, polyacrylamide, cellulose, or polyethylene, or combination thereof. For example, the biocompatible, synthetic scaffold may be a polymerized silicone. The biocompatible, synthetic scaffold may have a durometer of about 10 to 60. The composite graft may be porous or may have one or more porous regions. Alternatively, the composite graft may not be porous.

Additional features of the graft are set forth below. The deceased donor tissue may be at least one connective tissue, epithelial tissue, muscle tissue, or nervous tissue. The biological tissue component may be at least one of tissue particles, collagen fibers, or collagen particles. The composite graft may include at least one added protein, added cell, pharmaceutical agent, hydration-aiding compound, or combination thereof. The added protein may be a growth factor. The added cell may be a mesenchymal stem cell. The pharmaceutical agent may be an antibiotic, a pain-relieving medication, an anti-inflammatory, or combination thereof. The hydration-aiding compound may be a carboxymethyl cellulose. The biocompatible, synthetic scaffold may be water insoluble, non-biodegradable, or a combination thereof.

In another aspect, a method of treating a subject in need of an implant may include administering the composite graft described above at a delivery site in the subject. The composite graft may be selected based on at least one of the dimensions or the native tissue at the delivery site. The biological tissue component of the composite graft may be similar to the native tissue at the delivery site.

In another aspect, a method of manufacturing a composite graft may include (a) providing a biological tissue component obtained or derived from a deceased donor tissue; (b) combining the biological tissue component with a curing solution to form a composite mixture, the curing solution comprising at least one polymerizing agent; (c) disposing the composite mixture into a mold; and (d) curing the composite mixture for a predetermined period of time at a predetermined temperature to form the composite graft, the predetermined period of time at a predetermined temperature being sufficient to cause the polymerizing agent to polymerize into a synthetic scaffold, wherein the composite graft comprises the biological tissue component embedded in a synthetic scaffold.

Additional features of the method of manufacturing are set forth below. The mold used in the method may be configured to form a flat sheet of uniform thickness, a block, or an irregular pre-determined shape. The curing solution may include at least one hardening agent that facilitates polymerization of the polymerizing agent. A ratio of the hardening agent to the polymerizing agent may impact at least one of the flexibility, the compressibility, or the strength of the composite graft, wherein as the flexibility and the compressibility decreases and the strength increases as the ratio increases. The method may further include adding at least one additional component to the composite mixture, the additional component comprising an added protein, added cell, pharmaceutical agent, or hydration-aiding compound, or a combination thereof. The method may further or alternatively include combining the composite graft with at least one additional component, the additional component comprising an added protein, added cell, pharmaceutical agent, hydration-aiding compound, or a combination thereof. The method may further include shaping the composite graft into a final configuration.

In some instances, the method includes adding at least one soluble component to the composite mixture. The at least one soluble component may be a salt or a sugar, or a combination thereof. The method may further include removing the soluble component from the composite graft thereby creating voids in the composite graft, the removing comprising disposing the composite graft in a solution into which the soluble component will dissolve for a period of time sufficient to dissolve the soluble component.

Another aspect is a composite graft material may include a biological tissue component obtained or derived from a deceased donor tissue, and a polymerizing agent. The composite graft material may further include at least one of a hardening agent that facilitates polymerization of the polymerizing agent or an additional component comprising at least one added protein, added cell, pharmaceutical agent, or hydration-aiding compound.

In another aspect, a method of treating a subject in need of an implant may include administering the composite graft material described above at a delivery site in the subject.

In another aspect, a method of manufacturing a composite graft may include (a) providing a biological tissue component obtained or derived from a deceased donor tissue; and (b) combining the biological tissue component with a curing solution to form a composite mixture, the curing solution comprising at least one polymerizing agent. The curing solution may further include at least one of a hardening agent that facilitates polymerization of the polymerizing agent or an additional component comprising at least one added protein, added cell, pharmaceutical agent, or hydration-aiding compound.

The above described and many other features and attendant advantages of aspects and embodiments of the present invention will become apparent and further understood by reference to the following detailed description when considered in conjunction with the accompanying drawings.

DETAILED DESCRIPTION

This disclosure provides various systems and methods directed to a composite graft (also referred to herein as a composite implant or implant, among other nomenclature used herein). The flexible composite graft includes synthetic and biological tissue components. The biological tissue components may include at least one of tissue particles or a fibrous construct, such as collagen fibers and/or collagen particles. The biological tissue components may be obtained from a deceased donor or derived from deceased donor tissue. In some instances, a composite graft according to this disclosure may be appropriate for implantation into a subject in a region having a similar tissue type as the original donor tissue used as the biological tissue component or the original donor tissue from which the biological tissue component was derived. The terms patient and subject are used interchangeably in this disclosure.

The composite grafts, along with the systems and methods for making and using such grafts, as disclosed herein are useful in various industries including orthopedics, reconstructive surgery, podiatry, and cartilage replacement, for humans and for other species. Composite grafts may be used, for example, to replace damaged, removed, or degenerated fat pads (such as in the soles of the feet), damaged or degenerated bone, and damaged or removed muscle tissue or cartilage. It is contemplated that the combination of the synthetic component with the biological tissue component yields improved graft uniformity and flexibility over other currently known graft compositions. For instance, the systems and methods disclosed herein may utilize a tissue from a deceased donor, which can be in various shapes and sizes, to produce a composite graft that is more consistent and uniform in thickness, texture, composition, and/or surface texture, among other qualities. It is contemplated that the systems and methods for the flexible composite graft disclosed herein may increase yield in the production process by providing more uniform, customized, and predictable graft products. Also, the biological tissue component of the graft may increase the ability of the graft to be integrated into the implantation site of the patient, reducing risk of rejection or encapsulation. In some cases, the graft product may have a various porosity, thickness, and hardness (also referred to as flexibility), among other features, based on the desired use (e.g., implantation site). For example, such features may better mimic natural tissue function, natural appearance, or both, at the implantation site while offering the additional stability of the synthetic component.

Composite Grafts and Methods of Making

Figure 1:
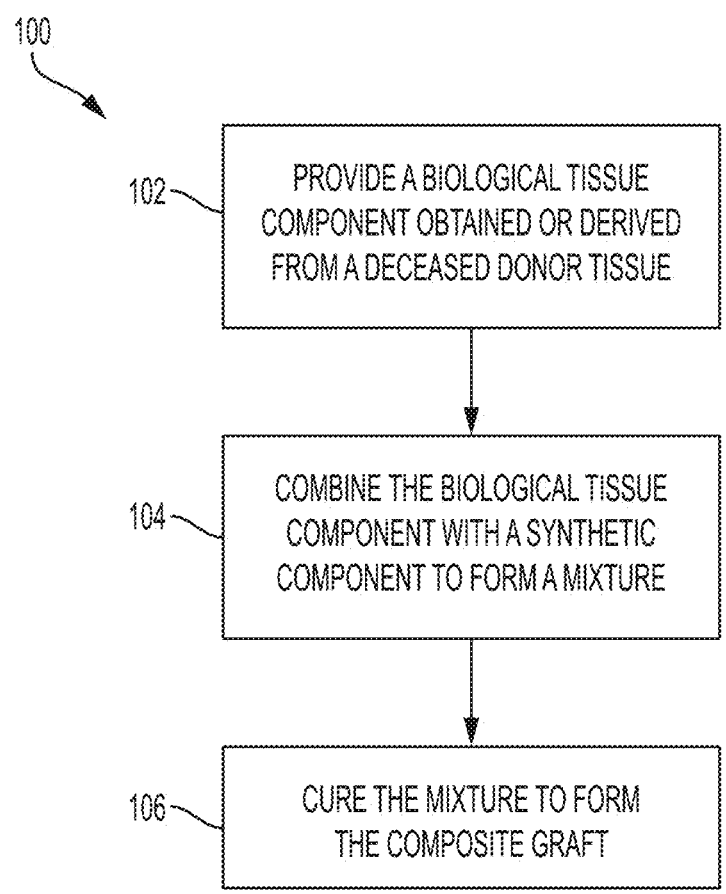
FIG. 1 illustrates a method of producing a composite graft, according to various aspects of the disclosure.

For illustrative purposes, FIG. 1 shows a method 100 of producing and implementing a flexible composite graft. It is contemplated that the method 100 may include any combination of the steps presented and in any order. Further, additional steps may be added and any of the steps may be optional. The method 100 may include providing a biological tissue component from a deceased donor tissue (step 102). In some instances, the biological tissue component is a portion of tissue. In some instances, the biological tissue component is derived from tissue obtained from the deceased donor. The deceased donor tissue may be processed, such as pulverized, morselized, and/or otherwise transformed into tissue particles and/or collagen fibers. Such processing may be based on characteristics of intended implantation site for the implant, such as a native tissue type at the implantation site of the patient, the tissue type of the deceased donor tissue itself, or both.

The method 100 may further include combining the biological tissue component with a synthetic component (step 104). In some examples, the liquid curing solution includes a two-part silicone composite. In one aspect, the method 100 may further include allowing the mixture of the biological tissue component and the synthetic component to cure (solidify) (step 106). Parameters for curing may be dependent on desired features of the composite graft. For instance, a duration of time for curing and/or a temperature of curing may be adjusted to achieve a particular degree of flexibility, or other adjustable quality in the composite graft. The nature of the synthetic component, such as chemical structure or its components, may be selected to achieve a particular degree of flexibility, or other adjustable quality in the flexible composite graft. Depending on the nature of the delivery site, the synthetic component may be selected to have a high degree of flexibility or a low degree of flexibility. Merely by way of example, a temperature-controlled curing process may allow for a temperature sensitive biological tissue component to be embedded in a permanent scaffold formed by the synthetic component, which can further be molded, cut, and manipulated to adjust the porosity of the implant, while retaining the activity or native features of the biological tissue component. Other steps may be included. For instance, a soluble component, such as a water-soluble salt, may be introduced to the mixture of the synthetic component and the biological tissue component prior to curing at step 106. In such cases, after curing at step 106, the soluble component may be dissolved (removed) rendering a porous composite graft. In another example, additional components, such as proteins, may be introduced into the mixture prior to, during, or after, curing at step 106, as further described elsewhere herein. For example, the additional components may be introduced into the mixture prior to curing, after curing, or both.

For illustrative purposes, the method 100 may further include implanting the composite graft at the delivery site (also referred to as an implantation site) of the patient (step 108). In some instances, prior to step 108, the composite graft may be cut or otherwise shaped to a final dimension or configuration suitable for the intended delivery site. In another aspect, the mixture of the synthetic component and the biological tissue component may be allowed to cure in a mold having the desired final dimensions or configuration. It is contemplated that the final dimensions or configuration correspond to physical dimensions of the delivery site of the patient where the composite graft is intended to be implanted. In some cases, a mold may have a negative or hollow cavity or recess into which the mixture is placed.

In another aspect, the method 100 may alternatively include delivering the mixture of the biological tissue component and the synthetic component to into the delivery site in the patient (step 108). In such instances, the mixture solidifies within the delivery site. The synthetic component may be selected to cure relatively quickly at body temperature. Depending on the nature of the delivery site, the synthetic component may be selected to have a high degree of flexibility or a low degree of flexibility.

Figure 2:
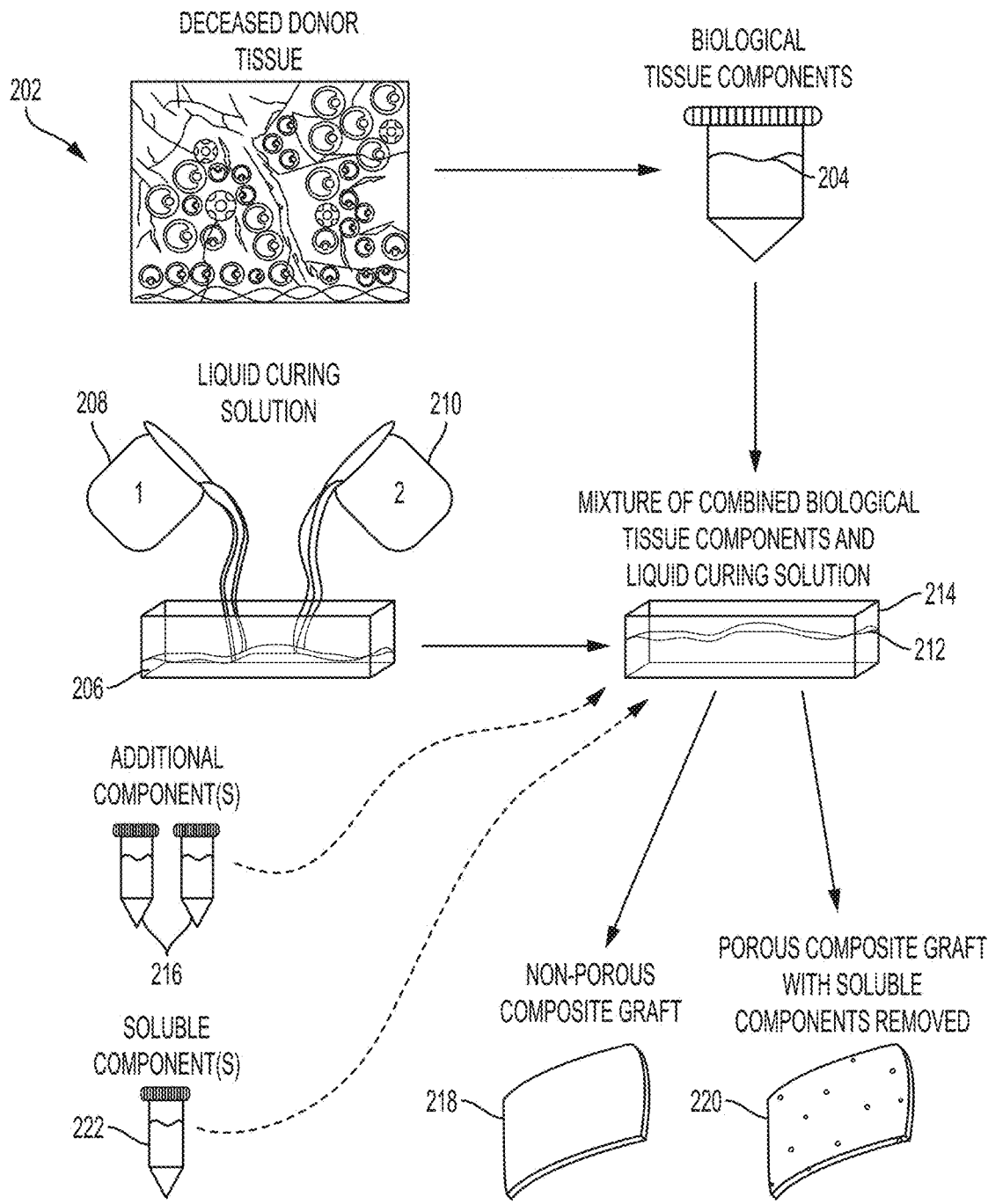
FIG. 2 illustrates aspects of a composite graft and methods of producing the composite graft, including representative components thereof, according to various aspects of the disclosure.

Turning now to FIG. 2, aspects of the composite graft and methods of producing such grafts, including representative components of the composite graft, are described. It is contemplated that the composite graft may include any combination of components presented in FIG. 2. Additional components and soluble components may be added, and any of the components may be optional. As shown in FIG. 2, deceased donor tissue 202 may be processed to provide the biological tissue component 204. In one aspect, the deceased donor tissue 202 may obtained from a human deceased donor or an animal deceased donor such as a mammalian deceased donor. Merely by way of example, the tissue of the deceased donor may comprise a connective tissue, an epithelial tissue, a muscle tissue, a nervous tissue. Exemplary connective tissue includes any of loose connective tissue, fat tissue, dense fibrous tissue, cartilage, bone, blood, and lymph. Exemplary muscle tissue include skeletal tissue, smooth tissue, and cardiac tissue. The tissue type of the deceased donor tissue 202 may be selected to correspond to a native tissue at an intended delivery site of a patient. For instance, if the composite graft is intended to be implanted at a delivery site having bone tissue, the deceased donor tissue 202 may also be bone tissue. Merely by way of example, the deceased donor tissue 202 may comprise demineralized bone, including cortical bone, cancellous bone, or both. The deceased donor tissue 202 may also be particulate donor tissue such as demineralized bone particles or minced cartilage. In one example, the deceased donor tissue can be processed to produce demineralized cancellous bone particles for use as the biological tissue component of the composite graft. In some instances, the composite graft may include a plurality of biological tissue components 204 obtained or derived from a plurality of different deceased donor tissues 202.

As further shown in FIG. 2, the deceased donor tissue 202 may be processed, transformed, or otherwise adjusted to provide the biological tissue component 204. The biological tissue component 204 may include ground tissue particles, a fibrous construct, e.g., collagen fibers, or a combination thereof. The biological tissue component 204 may include particles of various or uniform sizes. For example, the particles may be uniform in size or have a size in a defined range. In some instances, the average diameter of tissue particles may be about 0.01 mm to about 5 mm (e.g., about 0.01 mm, about 0.02 mm, about 0.03 mm, about 0.04 mm, about 0.05 mm, about 0.06 mm, about 0.07 mm, about 0.08 mm, about 0.09 mm, about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.5 mm, about 3.0 mm, about 4.0 mm, about 4.5 mm, or about 5.0 mm). In some instances, the particles have an average diameter of about 0.05 mm to about 1.1 mm, of about 0.5 mm to about 5 mm, of about 0.05 mm to about 2.5 mm, of about 1 mm to about 5 mm, or of about 1 mm to about 3 mm. Such particle sizes may differ based on the tissue type of the deceased donor tissue 202. In one instance, where the biological tissue component 204 is particulate bone tissue, the bone particles may be about 50 microns to about 1100 microns, and/or about 125 microns to about 1100 microns in average diameter. For example, particulate bone can be placed in a dual sieve apparatus, the upper sieve having 1100 micron diameter holes and the lower sieve having 50 micron diameter holes. Particles which pass through the upper sieve and which are retained by the lower sieve can be considered to have a particle size within a range from 50 to 1100 microns. Other sized sieves may be used to isolate particles in different size ranges for use at the biological component 204, and such a sieve apparatus may be used to sort other types of tissue particles as well. In another example, biological tissue component 204 may include fibrous tissue, e.g. collagen fibers isolated from deceased donor tissue. The majority of tissues in mammals contain collagen. In some instances, the length of the collagen fibers may be 0.1 mm to about 25 mm (e.g., about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 2.5 mm, about 3 mm, about 3.5 mm, about 4 mm, about 4.5 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm). In some instances, the length of the collagen fibers may be about 0.5 mm to about 10 mm, about 0.5 mm to about 5 mm, about 0.5 mm to about 3 mm, about 1 mm to about 5 mm, of about 1 mm to about 3 mm, about 5 mm to about 25 mm, about 10 mm to about 50 mm, or other size obtainable from deceased donor tissue. For example, the collagen fibers may be about 15 cm long or longer. In one example, biological tissue component 204 sized for replacing cartilage, for instance in a nose of a patient, may be about 0.5 cm long or smaller. Other sizes and/or size ranges may be contemplated where the biological tissue component 204 is processed or particulate deceased donor tissue or derivatives thereof.

In one aspect, the amount of the biological tissue component 204 may be about 5% to about 50% of the composite graft. For example, the biological tissue component 204 may be about 5%, 10%, 15%, 20%, 25%, 30%, 35%, 40%, 45%, or 50%. This proportion may be measured in terms of weight per weight (w/w) percentage or volume per weight (v/w) percent ($cm^3$ or mL). In some instances, dry tissue components, such as bone, bone particles, demineralized bone matrix (DBM) particles, collagen fibers, may be measured in terms of w/w percentage. In some instances, tissue particles, such as bone particles, DBM particles, minced cartilage, may be measured in terms of v/w percentage. In some instances, where the biological tissue component 204 is relatively stiff (non-compressible, strong), as the percentage increases, the stiffness (strength) of the composite graft increases and the compressibility (flexibility) decreases, and vice versa. In some instances, where the biological tissue component 204 is relatively compressible (flexible), as the percentage increases, the compressibility (flexibility) of the composite graft increases and the strength decreases, and vice versa.

In another aspect, the synthetic component is a polymerizing agent 208. As used herein, the term liquid curing solution 206 refers to one or more polymerizing agents 208 alone or in combination with one or more hardening agents 210. Exemplary polymerizing agents 208 include, but are not limited to, silicones, polyacrylamides, polyurethanes), celluloses, polyethylene, and polypropylene. The polymerizing agent 208 may contain a single type of chemical monomer or multiple monomer types (such as silicones of different molecular weights). Polymerization causes the polymerizing agent 208 to cure (harden/solidify). Some polymerizing agents polymerize without the addition of any additional agents, such as in response to time, temperature change, or other change in environmental factor, or a combination thereof. Exemplary self-polymerizing agents 208 are polyethylene and celluloses. Other exemplary self-polymerizing agents 208 are foamable polymers such as aerosol-based polyurethane. Other polymerizing agents 208 require the addition of one or more hardening agents 210 to facilitate polymerization (curing). In some instances, a hardening agent 210 may be referred to a cross-linker, cross-linking agent, an initiator, or a catalyst. As discussed elsewhere in this disclosure, time and temperature may be factors that influence cure rate. Different types of polymerizing agents 208 use different hardening agents 210 to facilitate polymerization (curing). Exemplary polymerizing agents 208 that use a hardening agent 210 include silicones and acrylates such as, for example, poly(methyl methacrylate) (PMMA). For example, silicones and acrylates may be cured using vinylmethylsiloxane copolymers as a hardening agent 210, an example of which is reinforced methyl vinyl dimethyl methylhydrogen siloxanes. In one aspect, the synthetic component is non-toxic, non-biodegradable/non-bioabsorbable. In another aspect, the synthetic component is highly water insoluble. In another aspect, the synthetic component may be highly erosion-resistant. In some instances, the type of polymerizing agent selected may influence the quality of the composite graft in terms of, for example, any of degree of flexibility (hardness), strength, and compressibility. In some instances, as the flexibility of the composite graft goes up, the strength of the graft strength may decrease, and vice versa. In some instances, as porosity of the composite graft increases, strength of the graft may decrease, and vice versa. The polymerizing agent used may be selected to set different ranges of hardness/stiffness/noncompressibility. For example, silicones have a lower stiffness range than polyurethane which in turn has a lower stiffness range than polyethylene.

FIG. 2 illustrates an exemplary two-part liquid curing solution 206 including a polymerizing agent 208 (such as silicone) and a hardening agent 210. A mixture ratio of a volume of the polymerizing agent 208 and a volume of the hardening agent 210 may be adjusted to achieve a particular quality of the composite graft such as, for example, a degree of flexibility, strength, compressibility, and/or hardness. Such qualities may further be manipulated by controlling a setting or curing time, temperature at which curing occurs, or both. In some instances, the ratio of polymerizing agent 208 to hardening agent 210 may be about 1:1, 2:1, 3:1, 4:1, 5:1, 6:1, 7:1, 8:1, 9:1, 10:1, 12:1, 15:1, 20:1, 30:1, or 50:1, or a ratios in this range. For example, in some instances, the ratio of polymerizing agent 208 to hardening agent 210 may be about 8:1, 9:1, 10:1, 12:1, or 15:1. The ratio is sufficient to result in complete polymerization of the polymerizing agent 208 after the period of curing. Undesirable ratios result in incomplete polymerization and may result in non-crosslinked monomers leaching out from the composite implant into the patient's body. In one example, the ratio of polymerizing agent to hardening agent is 10:1. In some instances, increasing the amount of hardening agent 210 in the liquid curing solution 206 may increase the final degree of hardness for the composite graft. In some cases, increasing the amount of hardening agent 210 in the liquid curing solution 206 may increase the rate of polymerization (hardening), and vice versa.

In some instances, the liquid curing solution 206 may be an off-the-shelf product. In some instances, the liquid curing solution 206 may be cured for about 1 min, 5 min, 10 min, 15 min, 20 min, 30 min, 1 hr, 2 hrs, 3 hrs, 4 hrs. 5 hrs, 10 hrs, 15 hrs, 24 hrs, or 48 hrs. In some cases, curing time may be within a range from about 5 minutes to about 48 hours. In some cases, the liquid curing solution 206 may be heated for a period of time. For example, heating may be performed for about 5 to about 10 minutes. In one aspect, the liquid curing solution 206 is non-reactive with the as the deceased donor tissue 202, the biological tissue component 204, and the native tissue at the intended delivery site of the patient. For example, where the polymerizing agent 208 is silicone, it is non-acidic (for example, it does not contain acetic acid).

Still in reference to FIG. 2, a mixture 212 may be produced that includes the liquid curing solution 206 and the biological tissue component (particles or fibers) 204 mixed thoroughly. In some instances, the mixture 212 may be placed in a mold 214 having the final dimensions or configuration that correspond to physical dimensions at the delivery site. In other instances, the mold 214 may be a container or tray that is not shaped to the physical dimensions of the delivery site. For example, the container or tray may be shaped to form a sheet or block. It is contemplated that the mixture 212 is cured in the mold 214 for a predetermined period of time and at a predetermined temperature. It is contemplated that the predetermined period of time and the predetermined temperature are interrelated settings that can be adjusted in order to achieve particular qualities of the composite graft. Further, it is contemplated that the curing time is dependent on an ambient temperature to which the mixture 212 is exposed. For example, as the temperature increases, the rate of polymerization generally increases as well. In some instances, the relationship of temperature to cure rate for a liquid curing solution 206 such as silicone may be defined by the formula $y=-0.1574x+27.934$, where y is the cure time (hours) and x is the cure temperature (° C.), as illustrated, for example, in FIG. 11A. Merely by way of example, a predetermined period of time may be about 24 hours at a predetermined temperature of about 25° C. In some instances, the predetermined temperature may be about 50° C. or less to protect the structural integrity of the biological tissue component 204. For example, proteins may begin to denature above about 50° C. In other instances, the predetermined temperature may be greater than 50° C. where the rate of curing of the mixture 212 is sufficiently rapid to minimize structural damage to the biological tissue component 204. For example, the predetermined period of time may be about 5 minutes and the predetermined temperature may be about 177° C. This feature may be particularly useful for large scale production of grafts (such as by quick injection molding). For example, a rapid cure rate of minutes results in a short time exposure of the biological tissue component 204 to high temperatures that may not result in significant collagen structure damage.

FIG. 2 shows that, optionally, one or more types of additional components 216 may be mixed into or otherwise introduced into the mixture 212 prior to, during, or after curing the mixture 212, or a combination thereof. Merely by way of example, the additional component 216 may include one or more proteins (such as growth factors), cells (such as stem cells), or pharmaceutical agents (such as, for example, an antibiotic, a pain-relieving medication, an anti-inflammatory, etc.). In some instances, such additional components 216 are added to the mixture prior to curing. Exemplary growth factors include one or more bone morphogenetic proteins (BMPs) and platelet-derived growth factor (PDGF). Such added components 216 may aid integration of the composite graft after it is implanted at the delivery site and, where a pharmaceutical agent is added, may provide slow-releasing chemicals to the delivery site to reduce incidence of pain, inflammation, infection, etc. In one example, cells may be added after the curing process. In some instances, the additional component 216 may be or include one or more hydration-aiding compounds. A hydration-aiding compound is one that can bind to water in its environment. An exemplary hydration-aiding compound is carboxymethylcellulose (CMC), which is generally considered safe for introduction into mammalian systems (e.g., by ingestion or injection). CMC is available in average molecular weights (MW) of 90,000 Daltons, 250,000 Daltons, and 700,000 Daltons. Each CMC molecular weight can be used by itself in a range of concentrations. Alternatively, a combination of multiple CMC molecular weights can be made and then the total concentration can be varied to find the ideal formulation. In some instances, a composite graft containing a hydration-aiding compound such as CMC may absorb water from the surrounding tissue at the implantation site, thereby swelling. The swelled graft may have an increased cushioning effect compared to an unswelled graft. In some instances, over time pressure may cause the graft to extrude water back into the surrounding tissue. It is contemplated that once pressure is released, over time the graft will again absorb water from the surrounding tissue. A contemplated use for such a graft would be as a cushioning implant in the sole of the foot. In some instances, the hydration-aiding compound is added to the mixture prior to curing.

Still referring to FIG. 2, a composite graft 218 produced by the above described curing process is shown. In one aspect, the composite graft 218 comprises a synthetic scaffold of the polymerized polymerizing agent 208 that contains and supports the biological tissue component 204. In one aspect, the flexible composite graft product 218 is a biocompatible, flexible synthetic scaffold containing a biological tissue component 204 (tissue particles or collagen fibers of or derived from a tissue of a deceased donor), wherein the tissue particles or collagen fibers, or both, are embedded in the synthetic scaffold by the curing process to form the graft. The composite graft 218 is removed from the mold 214 and either is, or may be, shaped to correspond to the delivery site. In that case, the flexible composite graft product 218 is ready to be implanted into a patient, and/or otherwise prepared for administration at the delivery site of a patient during a surgical procedure. The shape of the composite graft 218 may be rectangular, as shown in FIG. 2, and provide a particular surface area, thickness, and/or other measurement that is compatible with the physical characteristics of the delivery site. Other shapes and/or dimensions are possible (see FIGS. 5A-5C). The composite graft 218 may include one type of biological tissue component 204 or may contain a plurality of types of biological tissue components 204. In one aspect, the composite graft 218 may be water insoluble at the delivery site. In some instances, the graft may be resistant to erosion or degradation after implantation into a subject. For instance, the composite graft 218, and more particularly the synthetic scaffold component thereof (i.e. the cured polymerizing agent 208), may remain stable at a delivery site within the patient for the patient's lifetime as a permanent implant. In another example, the composite graft 218, and more particularly the synthetic scaffold component thereof, may not degrade or erode over a lifetime of the patient. In another example, the composite graft 218, and more particularly the synthetic scaffold component thereof, may be wear-and-tear free, e.g. does not break down from normal movement or breaks down very slowly over a lifetime of the patient. In some cases, the graft product may experience some degree of wear and tear following administration to the patient. In some cases, the composite graft 218 can be produced so as to exhibit a persistent or permanent quality at a certain temperature or temperature range, for example the body temperature of the recipient patient, following implantation into the patient's body.

In another aspect, as shown in FIG. 2, the composite graft 220 may be a porous structure. Such a configuration for the composite graft 220 may permit ingrowth of native tissue from the delivery site of the patient after implantation, e.g. during the lifetime of the patient. In some instances, such a configuration may permit retention of additional components 222 added to the composite graft after curing. Exemplary additional components 222 include one or more added proteins (such as growth factors), cells (such as stem cells), or pharmaceutical agents (such as, for example, an antibiotic, a pain-relieving medication, an anti-inflammatory, etc.). The synthetic scaffold component of the composite graft 220 may define at least one void configured to receive the native tissue of the patient at the delivery site. The native tissue may be a connective tissue, an epithelial tissue, a muscle tissue, and/or a nervous tissue. A porous composite graft 220 may be generated in different ways including, as discussed further below, adding one or more soluble components 222 to the mixture 212 before or during the curing process that may subsequently be removed or using a foamable polymer as the polymerizing agent 208, or a combination thereof may be used.

As mentioned, the porous structure 220 may be formed by adding one or more soluble components 222 to the mixture 212 before or during the curing process. Upon polymerization, the polymerizing agent solidifies into the synthetic scaffold of the composite graft 220 and is not water-soluble. For instance, the porous structure 220 may be formed by adding a fine powder of salt and/or sugar to the liquid curing solution 206, in addition to the biological tissue component 204, mixing the collective solution into a uniform mixture 212, placing the mixture 212 into a mold 214 for curing, and post curing, drawing out the salt and/or sugar by dissolution to create voids in the synthetic scaffold of the formed composite graft 220. For example, the cured composite can be treated with water such that the water-soluble components 222 (e.g., sugar, salt) is dissolved while the non-water soluble synthetic scaffold of the graft 220 is retained. Such dissolution may include further steps, such as washing, and/or wringing the composite graft 220 by squeezing the it in rollers, absorbent, and/or otherwise, to draw the water out. The soluble components 222 may be added before, during, after, or a combination thereof, addition of the biological tissue component 204. In some instances, the total surface area (porosity) may be controlled by the amount of soluble component 222 that is added to the liquid curing solution 206 (which is subsequently removed from the cured graft 220). It is contemplated that the random dispersion of salt, rather than a patterned dispersion thereof, may mimic biological patterns that are found at the delivery site. In some instances, the synthetic scaffold component of the composite graft 220 may define at least one void configured to receive additional components 222. In some instances, the mold may contain a patterned matrix of one or more plastic or metallic rods forming a grid or other pattern within the mold. After curing, the one or more rods may be removed from the composite graft thereby forming a matrix pattern of voids within the composite graft. In some instances, such voids may receive the soluble components 222, thereby providing a composite graft having soluble components 222 distributed therein in matrix pattern. Such components may be added before, during, after, or a combination thereof, curing of the liquid curing solution 206 into the composite graft 220. In one example, the composite graft 220 may be combined with additional components 222 after curing. In some instances, the additional components 222 may be water-soluble.

Also, as mentioned, the porous structure of the composite graft 220 may be formed by using a foamable polymer as the polymerizing agent 208. An exemplary foamable polymer is medical grade polyurethane, in particular an aerosol-based polyurethane. Initial quick expansion of the compressed aerosol may result in large pores with the composite graft 222, and escaping gas from the polymer during curing may form a plurality of micropores. The resulting composite graft 222 may be a semi-porous hard structure that is resistant to moderate forces and abrasion. In some instances, the cure rate may dictate the extent of micropore formation as a fast cure rate will limit micropore formation and a slower cure rate will provide time for the formation of more extensive dispersion of micropores.

The porosity of the composite graft 220 may be determined in various ways. For example, image analyzing software may be used to measure and quantitate the size and number of pores in images of the graft obtained by optical microscopy. Another way of measuring porosity is to measure water displacement by composite graft 220 before and after the soluble component(s) 222 are removed therefrom. The proportion to which less water is displaced by composite graft 220 after the soluble component(s) 222 relative to the amount displaced prior to removal of the soluble component(s) 222 reflects the degree of porosity of the composite graft 220.

Figure 3:
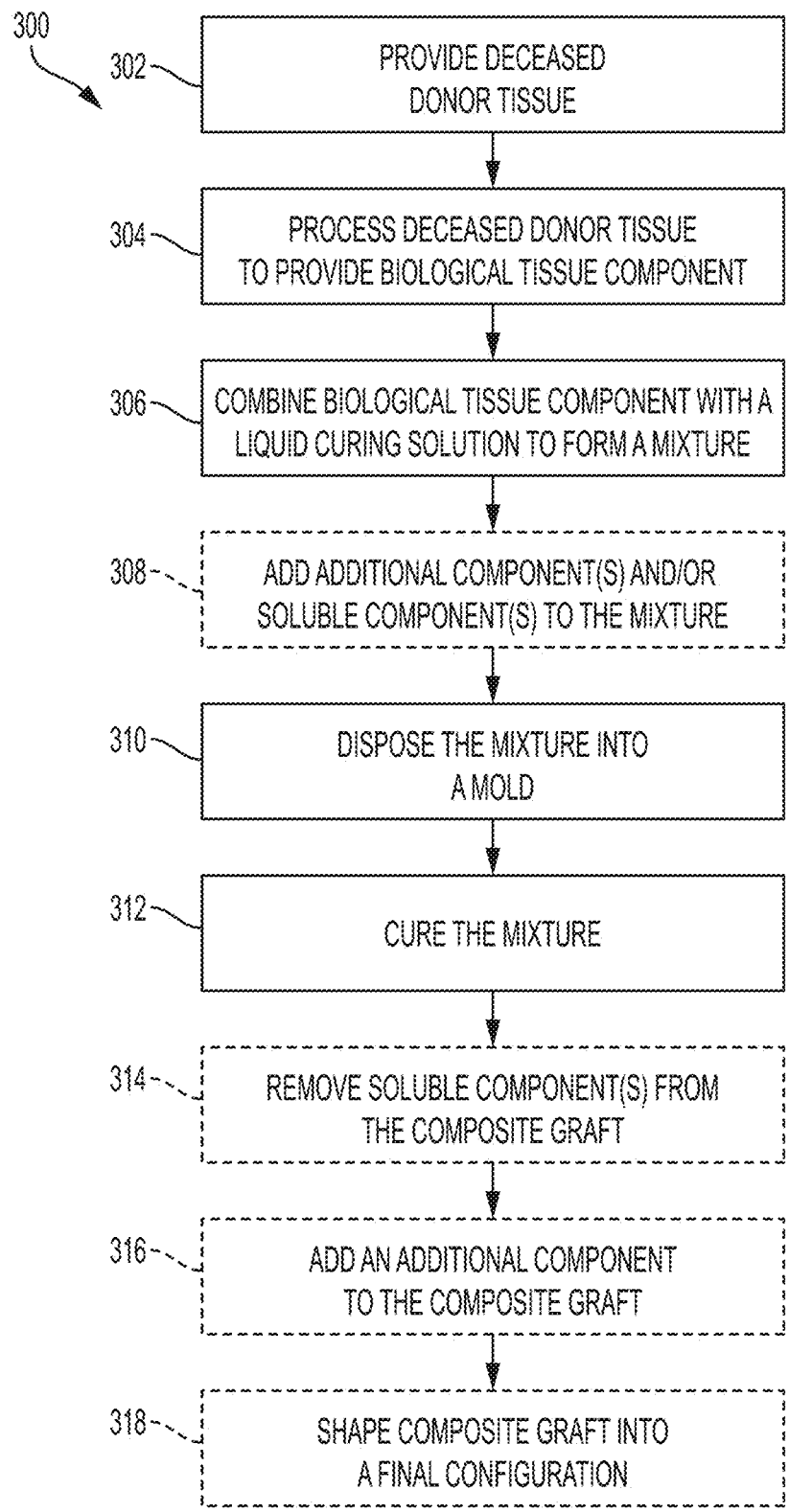
FIG. 3 illustrates another method of producing a composite graft, according to various aspects of the disclosure.

Referring now to FIG. 3, a method 300 for producing the composite graft 218 or 220, which may be solid or porous, is shown, and generally corresponds to the aspects of the grafts and methods of producing such grafts, including representative components thereof, described in FIG. 2. The method 300 may include one or more of the following steps for manufacturing the composite graft 218 or 220 having synthetic and biological tissue components for administration at a delivery site of a patient. It is contemplated that other steps may be added and any of the steps may be optional. The method 300 may include obtaining or providing a tissue graft, e.g. deceased donor tissue 202 (step 302). The method 300 may further include processing at least a portion of the deceased donor tissue 202 into a biological tissue component 204 (such as tissue particles, fibers) (step 304). Further, the method 300 may include combining at least a portion of the deceased donor tissue 202, the biological tissue component 204, or both, with a liquid curing solution 206 (step 306), to form the mixture 212. Forming the liquid curing solution 206 may include combining at least one polymerizing agent 208 and at least one hardening agent 210. In some instances, the liquid curing solution 206 is one or more polymerizing agents 208. Optionally, the method 300 may comprise adding additional components 216, soluble components 224, or a combination thereof, to at least one of the liquid curing solution 206, the mixture 212, or the biological tissue component 204. It is noted that any of the steps shown in FIG. 3 may be optional.

The method 300 may further include disposing the mixture 212 into a mold (step 310). In one aspect, the mixture 212 may be poured or spread into a mold 214. As discussed above, the mold 214 may be in a variety of different configurations and have a range of different dimensions. In some examples, the mold may have a void configured to form a flat sheet of uniform thickness or may be in the form of a block, or some other shape. In some instances, the mold is configured to have a void in the shape of the desired final composite graft 218 or 220. The method 300 may further include curing the mixture 212 into a cured composite graft 218 or 220 (step 312). Curing (polymerizing) of the polymerization agent 208 into a synthetic scaffold of the composite graft 218 or 220 may be performed over a predetermined period of time at a predetermined temperature. Further, the method 300 may include removing the soluble component(s) 222 that were added in step 308 from the cured construct (step 314). Merely by way of example, the method 300 may include creating pores in the composite graft 220 by dissolving the soluble component(s) 222. In one example, the soluble component(s) 222 may be water-soluble and may be removed from the composite graft 220 by soaking or otherwise combining the composite graft 220 with water for a period of time to dissolve the soluble component(s) 222. In some instances, the method 300 may include integrating an additional component 216 into the composite graft 218 or 220 post-curing. In some instances, the additional component 216 may be at least one of an added protein (such as growth factors), cells (such as stem cells), or pharmaceutical agents (such as, for example, an antibiotic, a pain-relieving medication, an anti-inflammatory, etc.) (step 316). The method 300 may further include further shaping of the composite graft 218 or 220 into a final desired configuration (step 318).

A feature of the disclosed composite grafts is that the physical properties may be selected based on the intended use, which relates to the nature of the delivery site in the patient. As discussed above, the physical properties of the composite graft may be determined by the synthetic component used (e.g., polymerizing agent 208, hardening agent 210), the biological tissue component 204, and any additional component 216 or soluble component 222 of the graft. In some instances, a graft having a high degree of flexibility may be suitable, while in other instances, a graft having a high degree of hardness may be suitable. In some instances, a porous graft may be suitable, such as where ingrowth of native tissue into the implanted graft is desired, or to serve as a mechanism to deliver additional components 216 in the graft to the delivery site. In some instances, a non-porous graft may be suitable. In some cases, a graft with a degree of compressibility may be suitable, while in other instances, a non-compressible graft may be suitable. Flexibility/hardness and compressibility are interrelated features, with increased flexibility promoting compressibility and increased hardness reducing compressibility. Increased porosity may, in some instances, also increase the graft's flexibility, compressibility, or both. In some instances, factors that influence the flexibility and compressibility include the type of polymerizing agent 208, the type of hardening agent 210, the amount of either the polymerizing agent 208 or the hardening agent 210, and the ratio of the polymerizing agent 208 and the hardening agent 210 to each other. For example, a contemplated polymerizing agent 208 is silicone, which is available in a range of different chemical structures and molecular weights. Different silicones have the ability to solidify to different degrees of hardness. In some instances, as increasing amounts of hardening agent 210 are used, the hardness of the synthetic scaffold of the graft increases. In some instances, a graft may include regions that are more flexible, more compressible, more porous, or a combination thereof, than other regions of the graft. This may be achieved by manipulating the components of the liquid curing solution 206 prior to, or during, the curing process. In some instances, features of the biological tissue component 204, such as type, amount, or both, may influence the hardness and/or compressibility of the graft. For example, a graft containing a high proportion of biological tissue component 204 may be less compressible and/or harder than a graft containing less biological tissue component 204. In some instances, a graft containing a biological tissue component 204 derived from bone may be less flexible, less compressible, or both, as compared to a graft containing a biological tissue component 204 derived from cartilage, adipose, or muscle. In some instances, features of the additional component 216, such as type, amount, or both, may influence the hardness and/or compressibility of the graft. For example, a graft containing a high proportion of additional component 216 may be less compressible and/or harder than a graft containing less additional component 216.

In one aspect, the hardness of the composite graft may expressed in terms of durometer. Durometer is a typical measure of hardness in polymers, elastomers, and rubbers. There are several scales of durometer, used for materials with different properties. The two most common scales, using slightly different measurement systems, are the ASTM D2240 type A and type D scales. The A scale is for softer plastics, while the D scale is for harder ones. However, the ASTM D2240-00 testing standard calls for a total of 12 scales, depending on the intended use; types A, B, C, D, DO, E, M, O, OO, OOO, OOO-S, and R. Each scale results in a value between 0 and 100, with higher values indicating a harder material. These scales are properly referred to as durometer types; i.e., a durometer type is specifically designed to determine a specific scale, and the scale does not exist separately from the durometer. Durometer, like many other hardness tests, measures the depth of an indentation in the material created by a given force on a standardized presser foot. This depth is generally dependent on the hardness of the material, its viscoelastic properties, the shape of the presser foot, and the duration of the test. ASTM D2240 durometers allow for a measurement of the initial hardness, or the indentation hardness after a given period of time. The basic test requires applying the force in a consistent manner, without shock, and measuring the hardness (depth of the indentation). If a timed hardness is desired, force is applied for the required time and then read. In some instances, the material under test should be a minimum of 6.4 mm thick. The final value of the hardness depends on the depth of the indenter after it has been applied for 15 seconds on the material. If the indenter penetrates 2.54 mm (0.100 inch) or more into the material, the durometer is 0 for that scale. If it does not penetrate at all, then the durometer is 100 for that scale. It is for this reason that multiple scales exist. Durometer is a dimensionless quantity, and there is no simple relationship between a material's durometer in one scale, and its durometer in any other scale, or by any other hardness test. In some instances, the polymerizing agent 208 used, when solidified, has a durometer in the range of about 10 to 100, or about 10 to 50, or about 30 to 70, or about 40 to 80. For example, the solidified polymerizing agent 208 may have a durometer of 10, 15, 20, 25, 30, 35, 40, 45, 50, 55, 60, 65, 70, 75, 80, 85, 90, 95, or 100. In one example, the polymerizing agent 208 is silicone and may have a durometer of between 10 and 65. In some instances, the silicone durometer is 40.

In another aspect, the flexibility of the composite graft may range from inflexible (having no flex/bendability) to highly flexible. In some instances, flexible composite grafts may bend in one or more regions. For example, a flexible graft may bend sufficiently to result in an angle of 1°, 2°, 5°, 10°, 15°, 25°, 30°, 40°, 50°, 65°, 75°, 90°, 100°, 120°, 130°, 150°, 170°, or in a range of about 1° to 170° in the graft as compared to the unbent graft (i.e. compared to the straight/chordline of the graft). In one example, a flexible graft may be folded such that distal regions of the graft are brought into contact.

In another aspect, the degree of compressibility of the composite graft may range from 0% (non-compressible) to about 90% of the original thickness of the graft. In one example, at 80% compressibility, the thickness of the graft may be reduced to a compressed thickness of 20% the original thickness of the graft. In some instances, the degree of compressibility of the graft may be 5%, 10%, 20%, 25%, 30%, 40%, 50%, 60%, 70%, 80%, 90%, or another degree within the range of 0% to about 90%.

In another aspect, the porosity of the composite graft may range from 0% porous (non-porous) to up to 80% porous. For example, the porosity of the composite graft may be 1%, 2%, 5%, 10%, 15%, 20%, 25%, 30%, 50%, 60%, 75%, 80%, or have another porosity within the range of 0% to about 80%.

Figure 4A:
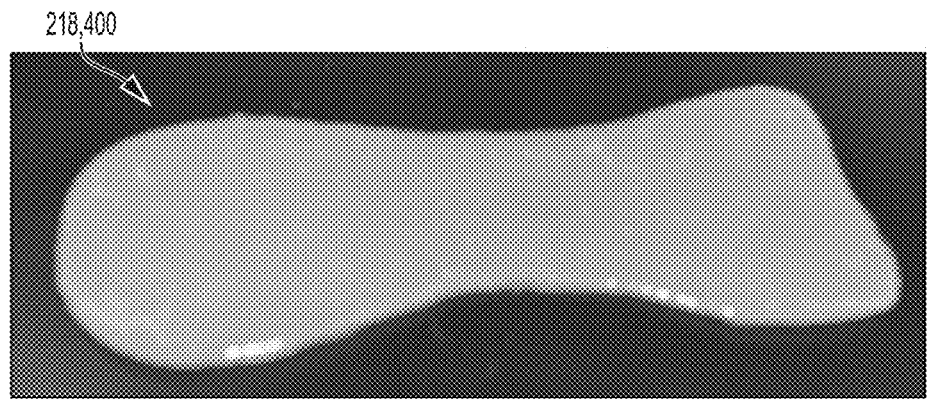
FIGS. 4A-4C illustrate examples of various shapes of a composite graft, according to various aspects of the disclosure.
Figure 4B:
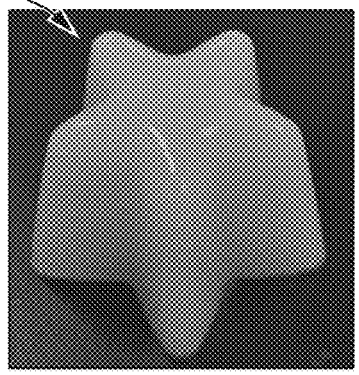
Figure 4C:
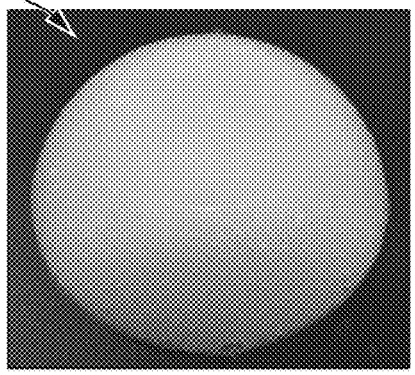

As discussed above, the composite graft 218 or 220 may be adjusted to provide various shapes and sizes by curing the mixture 212 in the mold 214 and/or by cutting the composite graft 218 or 220 to a final desired shape. Exemplary shapes are shown for graft 218 in FIGS. 4A-4C. Such shapes are also applicable for graft 220. Merely by way of example, FIG. 4A shows the composite graft 218 having an irregular shape as may be appropriate, in some instances, for use as a foot pad 400 implant. FIG. 4B shows the composite graft 218 shaped as a star 402. FIG. 4C shows the composite graft 218 shaped as a dome 404. The star 402 and the dome 404 grafts may be produced by molding, such as curing the mixture 212 in a plastic star-shaped or a dome-shaped mold 214, respectively. It is contemplated that the graft is easily extracted from the mold 214. In another aspect, shapes and sizes may be selected to correspond to dimensions of an anatomical body part, such as a hand or foot. In some applications, the mold may be obtained using 3D digital imaging, including MRI and CT scans, and/or 3D printing technology. A wide variety of other shapes and sizes for the grafts are contemplated.

In reference to FIG. 4A, in a particular example, the composite graft 218 may be shaped as a molded pad having a perimeter in a shape similar to the sole of a foot, e.g., the foot pad 400, for fat pad replacement purposes in the foot. The foot pad 400 may include a combination of a two-part silicone (liquid curing solution 206), adipose-derived collagen fibers (biological component 204), and carboxymethyl-cellulose (CMC) (additional component 216). It is contemplated that similar composite grafts may be applicable for a fat pad in a hand, or any other application. It is noted that CMC may absorb up to 1000 times its weight in water. The degree of absorption may depend on the molecular weight of the selected CMC. In practice, the CMC may absorb liquid once the graft, e.g., foot pad 400, is surgically implanted at the delivery site (i.e. the foot). The concentration and selection of the molecular weight of the CMC can be based on an amount of swelling desired such that the molded pad, e.g., the foot pad 400, provides sufficient thickness during the intended application, e.g., sufficient to withstand pressure during walking. Such stress-withstanding measures related to the foot pad 400 may have significantly less requirements for the palm and/or hand, which may experience a lesser amount of applied pressure. In practice, it is contemplated that if the patient is walking and starts to feel pain in the foot having the foot pad 400 implanted therein, the patient would merely need to sit down or otherwise relieve pressure on that foot to allow for the molded pad to re-absorb liquid to regenerate a swelled foot pad 400 to act as a cushion. Other and multiple applications of the present disclosure are readily apparent.

Figure 5:
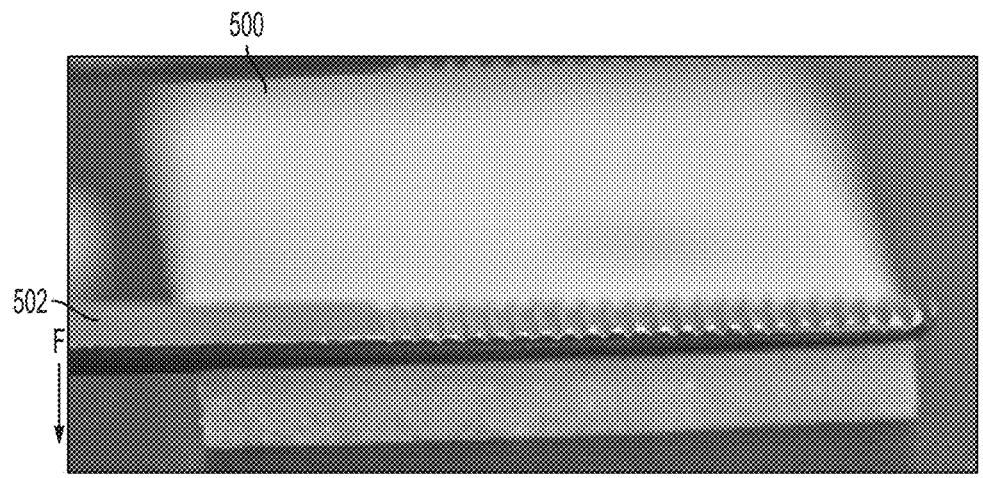
FIG. 5 illustrates an example of an incompressible, non-flexible composite graft, according to various aspects of the disclosure.

Turning now to FIG. 5, an example of an incompressible, non-flexible composite graft is shown, which may be referred to as composite graft 500. It is contemplated that the composite graft 500 may comprise any of the features and/or be similar to the composite graft 218 or 220 (see FIG. 2) except that its features result in incompressibility and inflexibility. As demonstrated in FIG. 5, an applied downward force F from a pressure-inducing instrument 502 does not cause any noticeable deformity or compression of composite graft 500. More particularly, an amount of force that composite graft 500 can withstand without deforming, and/or a degree of incompressibility of composite graft 500, may be manipulated and tailored for a specific application. For instance, changing features as described above regarding graft composition, or changing aspects of the curing procedure, may render different levels or degrees of incompressibility, flexibility, or both, for composite graft 500.

Figure 6A:
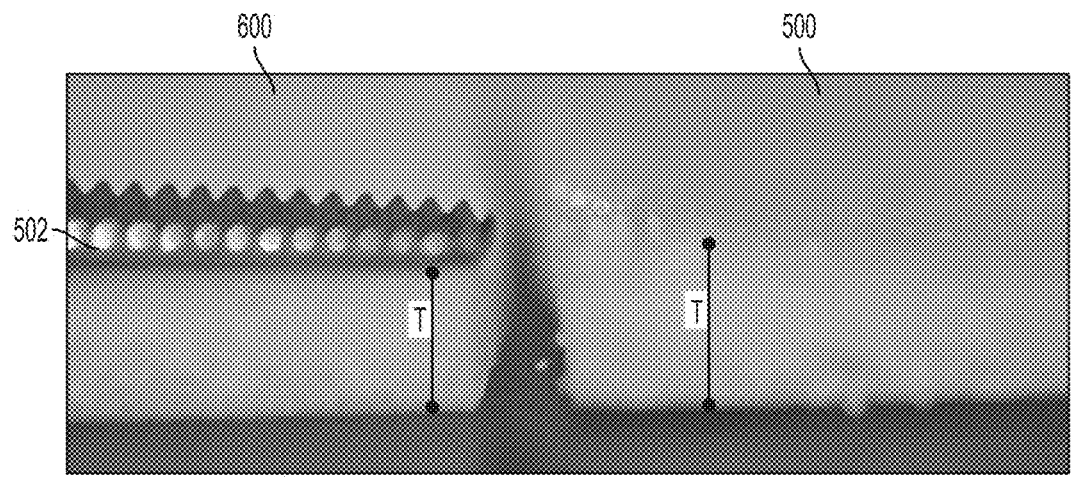
FIGS. 6A-6C illustrate an example of a compressible, porous, flexible composite graft, according to various aspects of the disclosure.
Figure 6B:
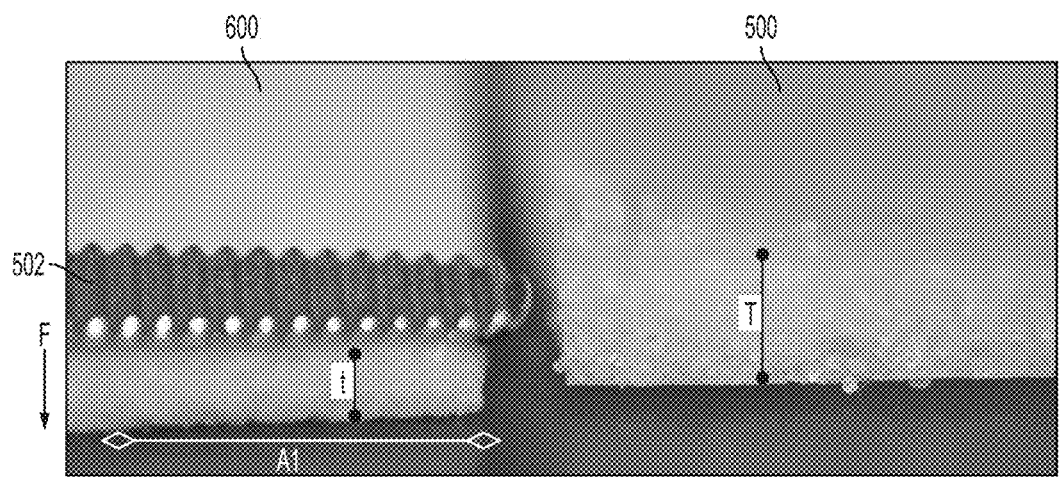
Figure 6C:
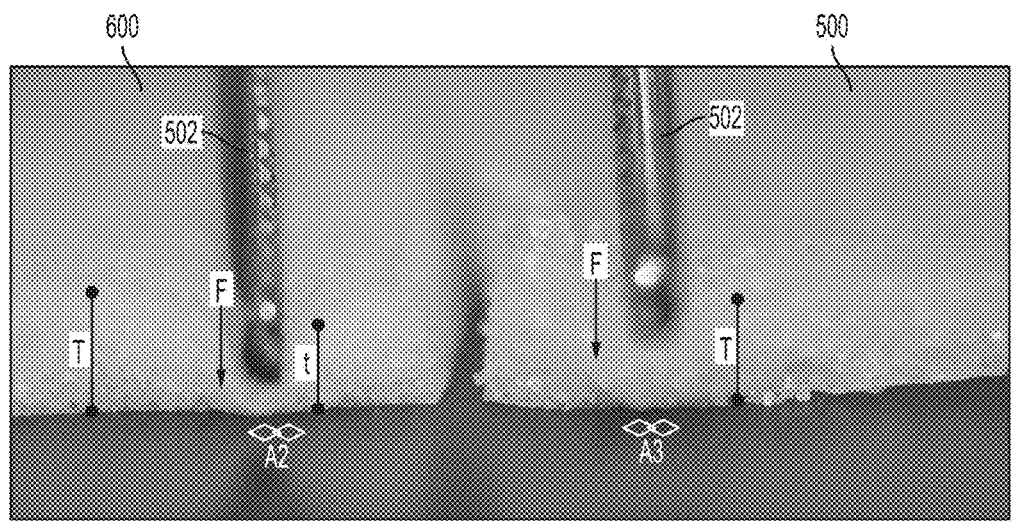

Referring now to FIGS. 6A-6C, an example of a porous, compressible, flexible composite graft is shown, which may be referred to as composite graft 600. It is contemplated that composite graft 600 may comprise any of the features and/or be similar to the composite graft 218 or 220 (see FIG. 2) except that its features result in compressibility and flexibility. FIGS. 6A-6C show side-by-side comparisons of composite graft 600 (left) and composite graft 500 of FIG. 5 (right) in various stress-applying situations. As shown in FIG. 6A, it is contemplated that composite grafts 500 and 600 have a similar initial, or original, thickness T. FIG. 6A illustrates a pre-compressed state of composite graft 600 in which the pressure-inducing instrument 502 does not impart any force, or a force that is significant enough, to compress or otherwise temporarily deform the grafts 500 and 600. Merely by way of example, small forces may cause less noticeable compression of composite graft 600 than larger forces. A degree of force that composite graft 600 can withstand without compressing may vary depending on a particular intended application of composite graft 600. Such degrees may be manipulated by changing features as described above regarding graft composition, or changing aspects of the curing procedure.

FIG. 6B demonstrates compression of composite graft 600 under the force F as applied by the pressure-inducing instrument 502. Application of the force F on an area A1 of composite graft 600 causes the original thickness T to reduce, temporarily, to a compressed thickness t, whereby T<t. It is contemplated that the thickness changes only under an area in which the force F is applied, such that remaining portions of the porous, compressible graft 600 that are not compressed comprises thicknesses greater than t and up to, and including, the initial thickness T. Further, the change in thickness may depend on the stiffness of composite graft 600, the amount of force F applied, or both. As mentioned previously, an amount of force that the porous, compressible graft 600 can withstand without deforming, or a degree of compressibility of composite graft 600, or both, may be manipulated and tailored for a specific application. For instance, changing features as described above regarding graft composition, or changing aspects of the curing procedure, may render various different levels of compressibility for composite graft 600. Composite graft 500 is shown in its original configuration next to composite graft 600 for comparison purposes. As shown in FIG. 5, application of force F to composite graft 500 does not alter its original thickness T.

FIG. 6C demonstrates another example of compression of composite graft 600 under the force F as applied at an area A2, which may be smaller or oriented differently than the area A1 of FIG. 6B. As shown in FIG. 6C, application of the force F on the area A2 of composite graft 600 causes the original thickness T to reduce, temporarily, to the smaller compressed thickness t, while remaining uncompressed portions of composite graft 600 are generally unchanged in thickness, barring an immediate region surrounding the depression area A2. FIG. 6C further demonstrates that when the same force F is applied by the pressure-inducing instrument 502 at an area A3, which may be similar to the area A2, of composite graft 500, no significant compression, or a lesser degree of compression, is imparted. Merely by way of example, T may be about 3 mm to 7 mm, and t may be about 0.5 mm to about 2 mm. In some aspects, T may be about 5 mm and t may be about 1 mm. In some instances, the thickness of composite graft 600 may change by about 80% upon a maximum compression.

Figure 7A:
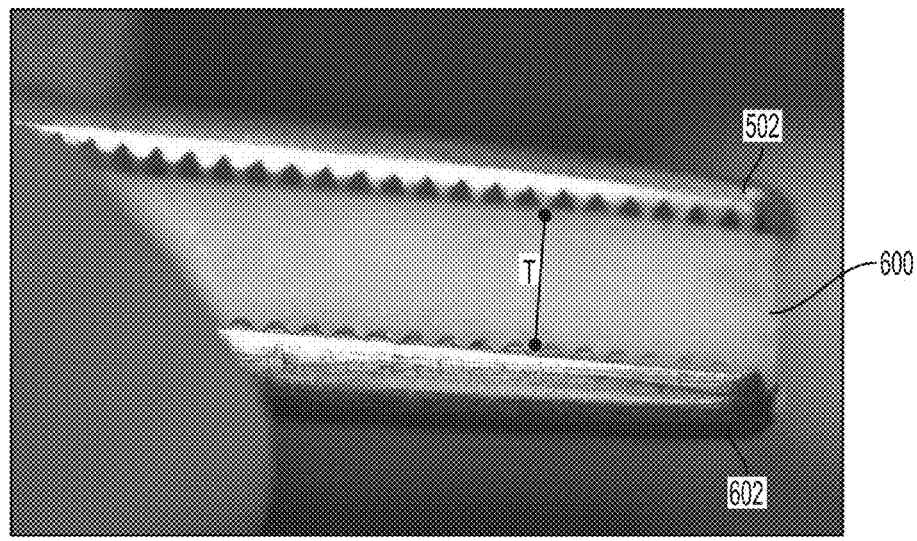
FIGS. 7A-7B illustrate examples of a degree of compression for the composite graft of FIGS. 6A-6C, according to various aspects of the disclosure.
Figure 7B:
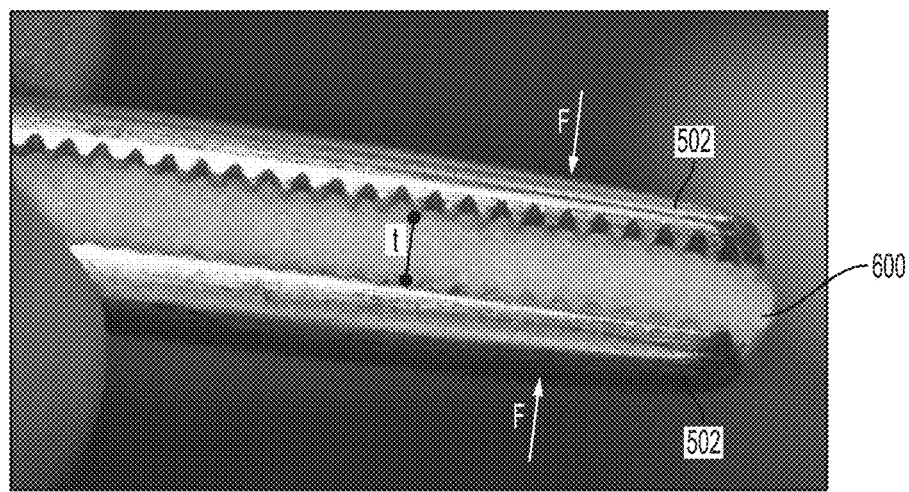

FIGS. 7A-7B show further examples of a degree of compression for composite graft 600. More particularly, FIG. 7A shows composite graft 600 provided between two pressure-inducing instruments 502 in a pre-compressed stage, whereby no significant force is applied and the original thickness T is defined. FIG. 7B illustrates a compressed stage, whereby composite graft 600 is compressed under force(s) F applied by one or both of the pressure-inducing instruments 502. In one example, composite graft 600 is compressed by opposing or counteracting forces F on opposing sides of composite graft 600 to define a smaller thickness t. The degree of compression may be about sufficient to compress into and fill up a void at an implantation site. It is contemplated that FIGS. 7A-7B may illustrate a maximum degree of compression, which may be about 80%, for a composite graft 600 having a particular graft composition and made using a particular curing procedure.

Figure 8A:
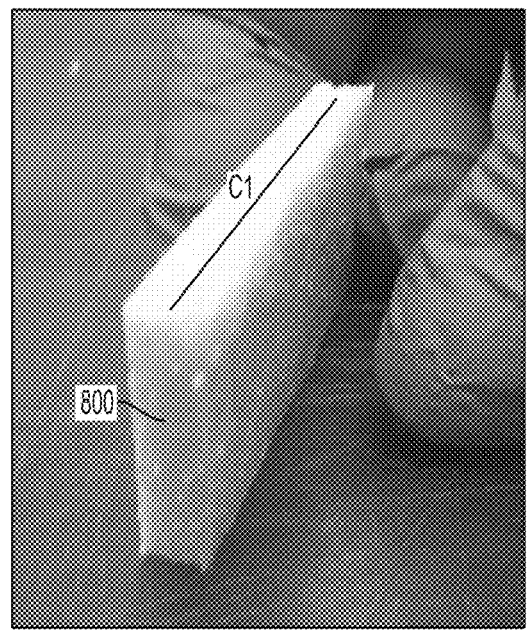
FIGS. 8A-8B illustrate another example of a flexible composite graft, according to various aspects of the disclosure.
Figure 8B:
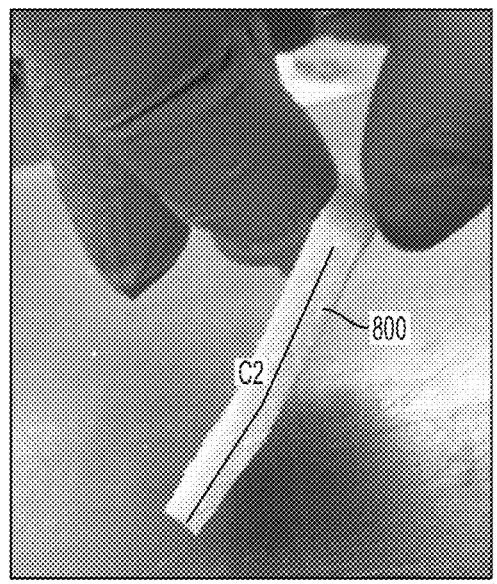
Figure 9A:
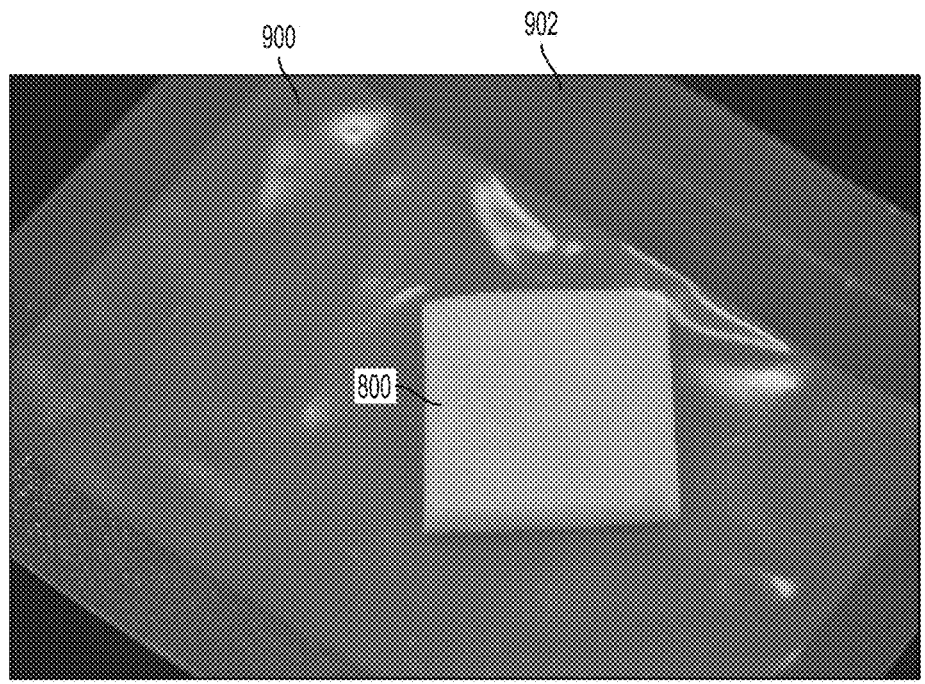
FIGS. 9A-9B illustrate an example of the flexible composite graft disposed in a sleeve, according to various aspects of the disclosure.
Figure 9B:
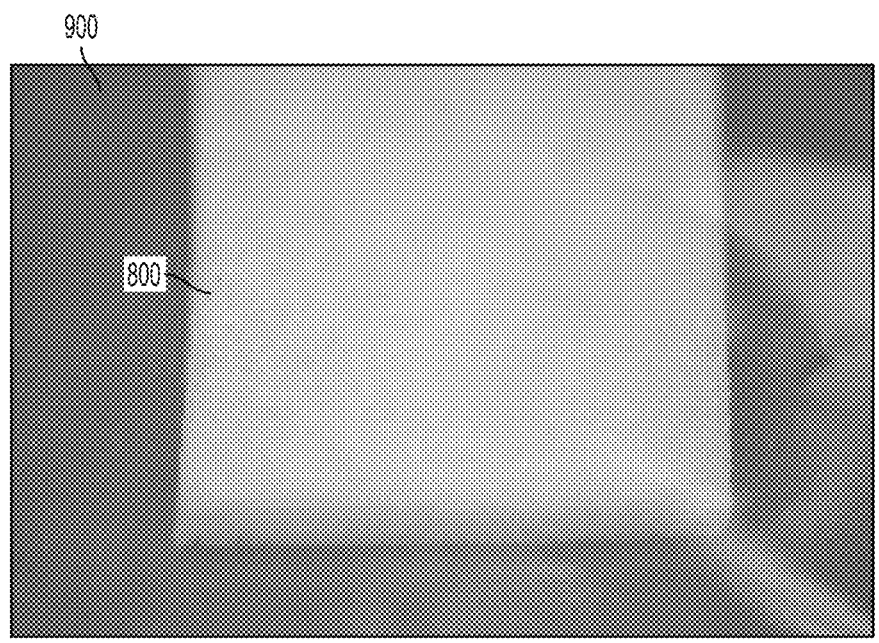

FIGS. 8A-8B show an example of flexibility of a composite graft 800, which may be any of composite graft 218, composite graft 222, or composite graft 600. FIG. 8A shows the composite graft 800 that is generally rectangular-shaped and not flexed or not withstanding any flexure pressure. It is noted that other shapes are possible. As shown in FIG. 8A, a straight chordline C1 is defined by an edge or thickness of the composite graft 800 in the unflexed state. FIG. 8B shows a flexed state of the composite graft 800, whereby a curved chordline C2 is defined by the same edge (as that of C1). It is contemplated that the degree of curvature may vary depending on a bending force imparted and/or an amount of flexibility provided by the composite graft 800, which may be adjusted by changing the components of the graft (before, during, after curing), the curing process of the mixture 212, or both. Further, it is contemplated that the composite graft 800 is resilient and may return to the unbent state after removing the bending force. FIGS. 9A-9B depict the composite graft 800 in a square, slab-like configuration. The composite graft 800 is shown in a plastic sleeve 900 having a seal 902.

Methods of Treatment

Provided herein are methods of using the composite grafts described in this disclosure for treating patients. Useful applications of the composite grafts include orthopedics, reconstructive surgery, podiatry, and cartilage replacement. The composite grafts may be implanted into a patient's body at a site in which the native tissue, for example, has been removed, is damaged, or is degenerated. As discussed herein, the composite graft may be in a configuration suitable for implantation or may be shaped prior to implantation into a suitable shape. Also, as discussed herein, the composition of the composite graft may be selected based on the nature of the implantation site, in terms of the type of biological tissue component 204, the synthetic component 208, the components of the liquid curing solution 206, and the components of the mixture 212, including any additional components 216 and soluble components 222. In addition, as discussed herein, the physical properties of the composite graft may be selected based on the intended use, in terms of, for example, the degree of porosity, flexibility, and compressibility. Exemplary uses for the composite grafts described herein are for cartilage replacement implants, breast implants, hand or foot fat pad replacement implants, muscle implants, amongst others.

Figure 10A:
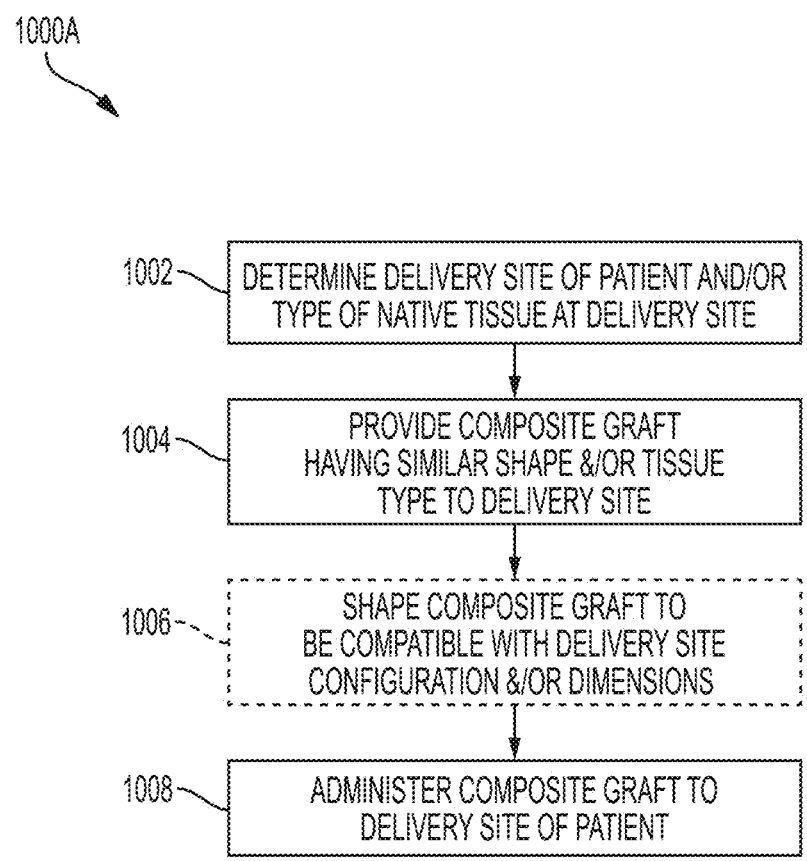
FIG. 10A-10B illustrates methods of treatment using a composite graft, according to various aspects of the disclosure.

In reference now to FIG. 10A, a method 1000A of treatment using the composite graft 218 or 220 is shown. The method 1000A may include any combination and order of the steps shown in FIG. 10A. Further, additional steps may be contemplated and any of the steps may be optional. The method 1000A may include determining at least one of a delivery site for the patient and a native tissue type at the delivery site of the patient (step 1002). Step 1002 may entail determining various measurements at the delivery site, which may be utilized to define measurements of the composite graft 218 or 220, such as a thickness, surface area, surface texture, and other measurements. For example, the delivery site may include a gap or void in the native tissue, such as a defect or damaged site, or site from which native tissue has been removed. In some aspects, step 1002 may include medical imaging, such as any of X-ray imaging, MRI scans, or CT scans, that provide dimensions, which may be utilized for making molds for curing the composite graft 218 or 220.

The method 1000A may further include providing the composite graft 218 or 220 in which the biological tissue component 204 that is deceased donor tissue 202, or derived from deceased donor tissue 202, is similar to the determined native tissue type at the delivery site of the patient (step 1004). For example, if the delivery site is in a region of bone, the biological tissue component 204 of the composite graft 218 or 220 may be bone or bone-derived. In similar examples, the biological tissue component 204 may be muscle or adipose tissue, or derived therefrom, where the delivery site includes muscle or adipose tissue. In some instances, the method 1000A further includes shaping the composite graft 218 or 220 to be compatible with a shape of the delivery site (step 1006). It is contemplated that the composite graft product 218 or 220 may be shaped multiple times, such as cut, bent, folded, and the like, at step 1006. Further, the method 1000A includes administering the composite graft 218 or 220 at a delivery site of the patient (step 1008). In some aspects, the delivery site includes a bone, a joint, a cartilage, a skin, and/or a muscle surface. In another aspect, the delivery site may include a space that may be a tumor or previously occupied by a tumor, such as a breast or bone tissue implantation site, or other site related to reconstructive surgery applications such as, for example, wound sites or sites where native tissue has degraded. For instance, the composite graft 218 or 220 may be used as a cartilage replacement to maintain a structural shape (such as for nose reconstruction, ear configurations) or function (such as for ACL replacement), a bone replacement (such as for ribcage reconstruction), an adipose tissue replacement (such as for breast reconstruction or fat pad replacement such as in a hand or foot). In some cases, such as fat pad replacement in a palm or foot, a more compressive or stress-withstanding material for the composite graft 218 or 220, and more particularly for the synthetic scaffold thereof, may be utilized, as described elsewhere herein. In some instances, the composite grafts described herein can be used as a structural filler for voids or divots (e.g., tissue voids or divots in the same tissue type as the biological tissue component 204) and may not erode away or degrade.

Figure 10B:
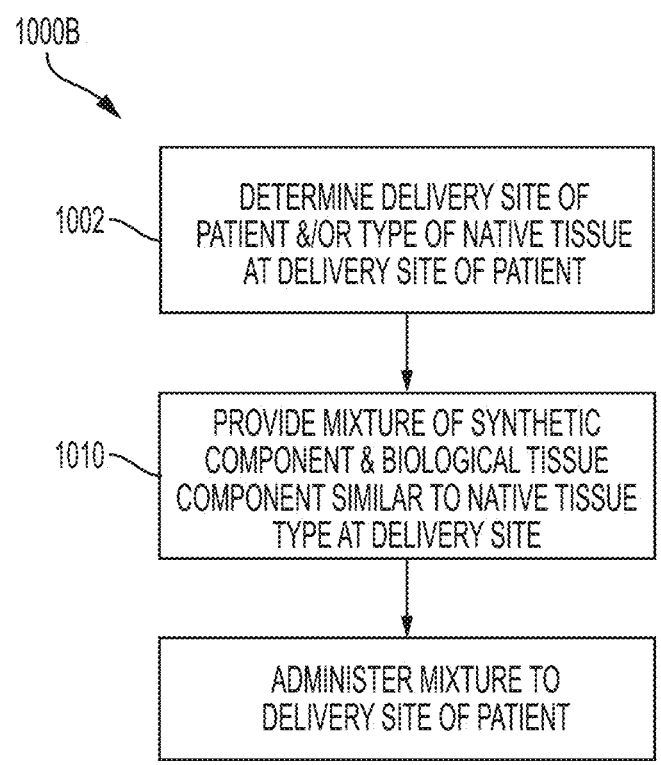

In reference now to FIG. 10B, a method 1000B of treatment using a modified version of the composite grafts described herein is described. The method 1000B may include any combination and order of the steps shown in FIG. 10B. Further, additional steps may be contemplated and any of the steps may be optional. The modification to method 1000B compared to method 1000A is that the mixture 212 is injected into the delivery site of the patient and cures in situ into the composite graft. The method 1000B may include step 1002 as described for FIG. 10A of determining at least one of a delivery site for the patient and a native tissue type at the delivery site of the patient. The method 1000B may further include providing the mixture 212 in which the biological tissue component 204 that is deceased donor tissue 202, or derived from deceased donor tissue 202, is similar to the determined native tissue type at the delivery site of the patient (step 1010). The features described above with respect to step 1006 are generally applicable for step 1010 as well. Further, the method 1000B includes administering the mixture 212 at a delivery site of the patient (step 1012). In some instances, a hardening agent 210 may be added to the mixture 212 prior to its administration at the delivery site to facilitate curing. In some instances, the mixture 212 may include a self-polymerizing polymerizing agent 208. In some instances, it may be difficult to determine the measurements at the delivery site, or fixed measurements may not be necessary. In such instances, it may be that the delivery site is visually inspected at the time of surgery and during delivery of the mixture 212 to determine the appropriate amount to be delivered. Exemplary delivery sites for method 1000B include, but are not limited to, lips, cheeks, hands, and breast.

Experimental Procedure

The grafts shown in FIGS. 4A-4C, 5, 6A-6C, 7A-7B, 8A-8B, and 9A-9B are all two-part silicone formulations poured into a mold or a flat sheet of uniform thickness then cut to squares in a manner similar to that described below for the graft shown for FC1 in FIG. 11A. The compressible grafts were achieving by adding salt as a soluble component in a manner similar to that described below for FC2 in FIG. 11B.

In one example, a flexible composite graft product was developed using a liquid silicone rubber composed of a two-part liquid curing solution 206: Liquid Silicone Rubber (LSR) Implant Grade 40 Durometer as the polymerizing agent 208 and reinforced methyl vinyl dimethyl methylhydrogen siloxanes as a hardening agent 210 (LSR System from Applied Silicon, Santa Paula, Calif.). Silicone rubber is a long-term implantable material generally considered safe and non-toxic. The two liquid curing solution 206 included 10 parts of the silicone and 1 part of hardening agent (mixture ratio of 10:1). More particularly, 53.61 g or 50 mL of the silicone and 4.69 g or 5 mL of hardening agent were combined and mixed thoroughly with a spatula. Subsequently, 25.25 g of demineralized bone matrix (DBM) particles (biological tissue component 204) were mixed into the liquid curing solution 206 to form a mixture 212. The combined mixture was about 83.55 g, and 36.99 g of the combined mixture was separated and set aside (herein referred to as "FC1"). The remaining 46.56 g of the combined mixture (herein referred to as "FC2") was mixed thoroughly with about 20.38 g of NaCl (soluble component 222) to be removed after curing to generate a porous graft 220. The FC1 was spread out evenly in an acrylic dish to a thickness of about 0.5 cm. The FC2 was handled in a similar manner.

Figure 11A:
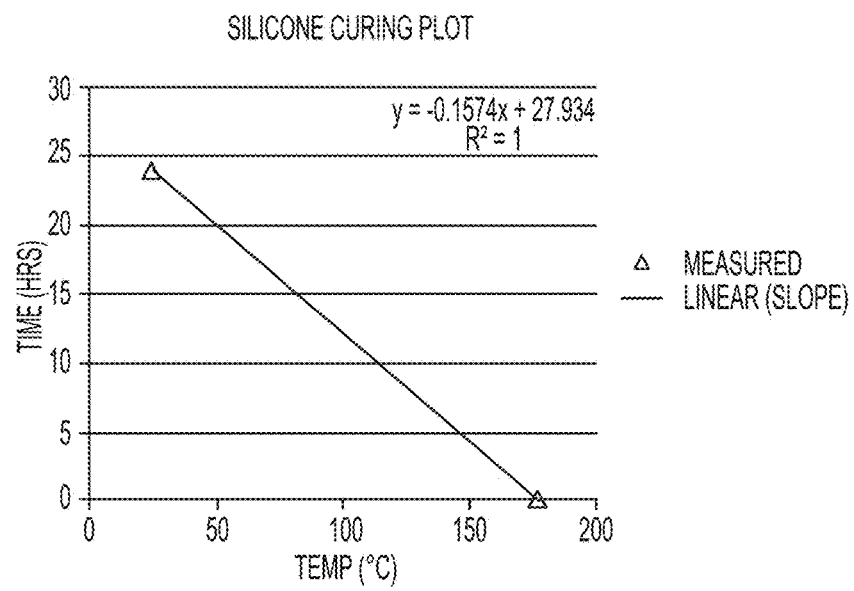
FIGS. 11A-11D illustrate a silicone curing plot and aspects of experimentally-produced grafts, according to various aspects of the disclosure.
Figure 11B:
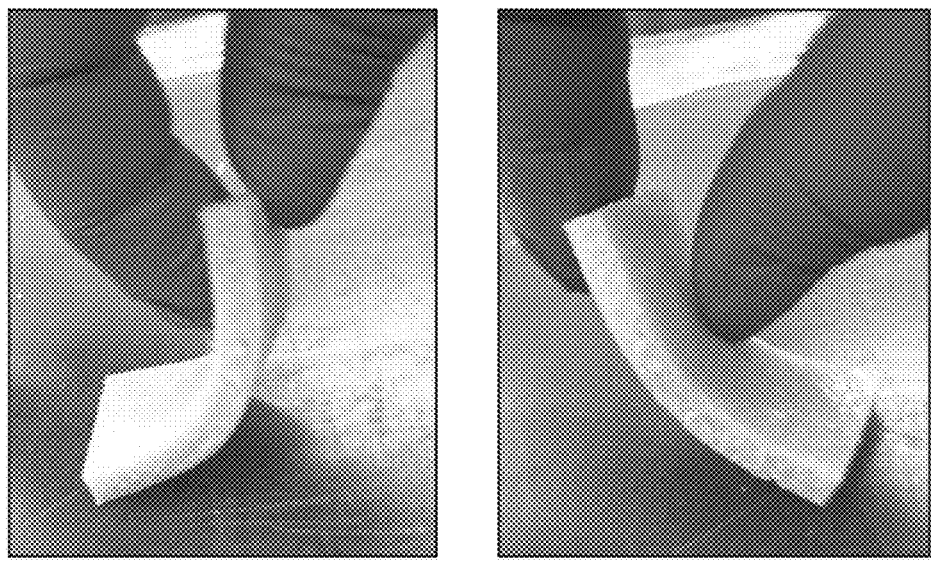
Figure 11C:
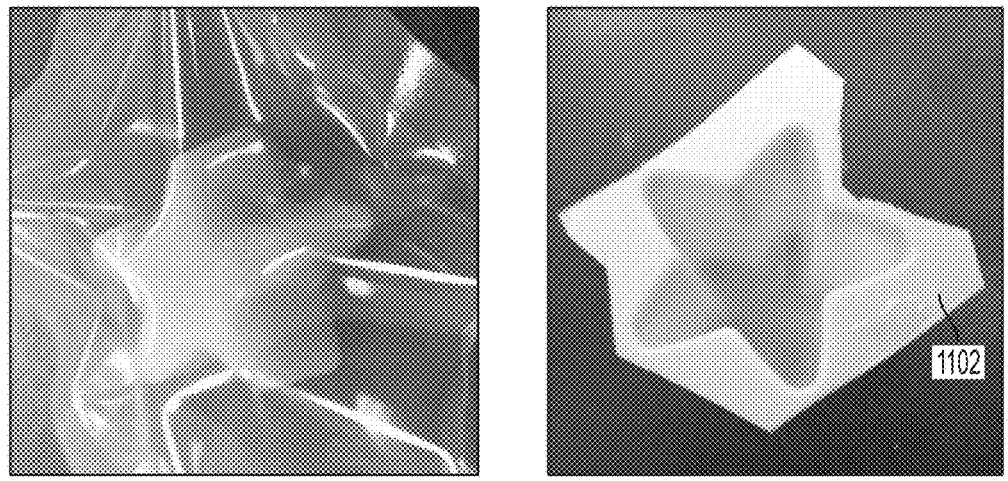

Turning now to FIG. 11A, a silicone curing plot having temperature (° C.) on the x-axis and time (hours) on the y-axis was provided, or otherwise extrapolated to determine a length of time for curing the silicone at a desired 60° C. For instance, as shown, the linear plot was provided having predetermined, or otherwise known, endpoints where at 25° C. the curing time is about 24 hours, and at 177° C. the curing time was about 5 minutes or 0.08 hours. The linear equation describing the such plot is determined as $y=-0.1574x+27.934$. Taking $x=60$ and solving for y, the equation yielded $y=18.49$ hours. Therefore, the FC1 and FC2 were incubated for about 18.49 hours at 60° C. After curing, the FC1 and FC2 slabs were removed from the acrylic dishes. The cured grafts were very flexible, as demonstrated in FIG. 11B. The slabs were cut into strips that easily folded onto themselves, further demonstrating flexibility. In another example, as shown in FIG. 11C, a portion of the FC1 was molded into a star-shaped graft using a star-shaped plastic mold 1102. The flexibility of the cured synthetic scaffold (polymerized silicone rubber) allows for the star-shaped graft to be easily extracted from the star-shaped mold 1102, and would similarly be easily removable from other molds having intricate shapes and corners. The FC2 was treated to remove the salt content by dissolution in water and checked for porosity. The dissolution was performed by submerging the cured silicone structure in purified water with stirring and intermittent water exchanges with fresh purified water until a final purified water sample showed minimal salt traces upon moisture evaporation. The porosity was empirically determined by adding increasing amounts of salt to uncured silicone and performing the above salt removal post curing to find the ideal porosity which will be correlated to a compressibility index.

Figure 11D:
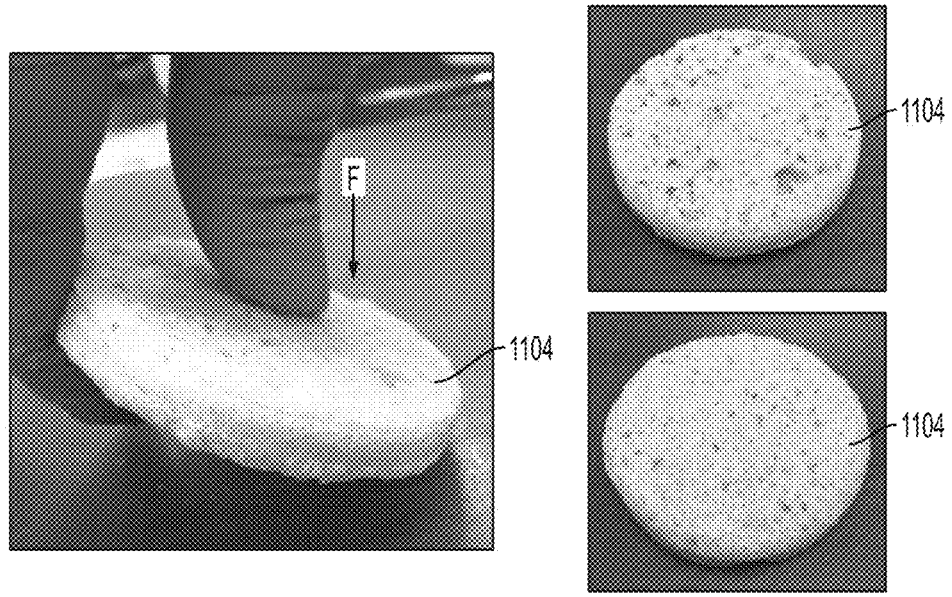

As a comparison, FIG. 11D illustrates another experiment that produced a composite graft 1104 made from a foaming polyurethane (polymerizing agent 208) and ground, cancellous bone particles (biological tissue component 204). As shown in FIG. 11D, the mixture 212 hardened into a hard configuration with no flexibility. For instance, upon application of the force F, the composite graft 1104 demonstrates an unbending stiffness yet is porous, having a plurality of different sized pores defined therein.

All patents, patent publications, patent applications, journal articles, books, technical references, and the like discussed in the instant disclosure are incorporated herein by reference in their entirety for all purposes.

It is to be understood that the figures and descriptions of the disclosure have been simplified to illustrate elements that are relevant for a clear understanding of the disclosure. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments, such substitution is considered within the scope of the disclosure.

The examples presented herein are intended to illustrate potential and specific implementations of the invention. It can be appreciated that the examples are intended primarily for purposes of illustration for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Aspects and embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

While exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A composite graft, comprising:
    a biocompatible, synthetic scaffold; and
    a biological tissue component obtained or derived from a deceased donor tissue, wherein the biological tissue component is embedded in the biocompatible, synthetic scaffold, wherein:
        the composite graft is porous or has one or more porous regions,
        the biological tissue component comprises bone particles, cartilage particles, or collagen particles,
        the biological tissue component comprises particles having an average diameter from 0.01 mm to 5 mm, and
        the particles are embedded in the biocompatible, synthetic scaffold, and
        the composite graft is formed by:
            combining the biological tissue component with a curing solution to form a composite mixture, the curing solution comprising at least one polymerizing agent,
            disposing the composite mixture into a mold, and
            curing the composite mixture for a predetermined period of time at a predetermined temperature to form the composite graft, the predetermined period of time at a predetermined temperature being sufficient to cause the polymerizing agent to polymerize into the biocompatible, synthetic scaffold, wherein the polymerizing agent, when solidified, has a durometer in the range of between 10 and 65.

2. The composite graft of claim 1, wherein the biocompatible, synthetic scaffold comprises a polymerized silicone, polyacrylamide, cellulose, or polyethylene, or combination thereof.

3. The composite graft of claim 1, wherein the biocompatible, synthetic scaffold comprises a polymerized silicone.

4. The composite graft of claim 1, wherein the deceased donor tissue comprises at least one connective tissue, epithelial tissue, muscle tissue, or nervous tissue.

5. The composite graft of claim 1, wherein the composite graft comprises at least one added protein, added cell, pharmaceutical agent, hydration-aiding compound, or combination thereof.

6. The composite graft of claim 5, wherein the added protein is a growth factor.

7. The composite graft of claim 5, wherein the added cell is a mesenchymal stem cell.

8. The composite graft of claim 5, wherein the pharmaceutical agent is an antibiotic, a pain-relieving medication, an anti-inflammatory, or combination thereof.

9. The composite graft of claim 5, wherein the hydration-aiding compound comprises a carboxymethyl cellulose.

10. The composite graft of claim 1, wherein the biocompatible, synthetic scaffold is water insoluble, non-biodegradable, or a combination thereof.

11. A method of treating a subject in need of an implant, comprising administering the composite graft of claim 1 at a delivery site in the subject.

12. The method of claim 11, wherein the composite graft is selected based on at least one of the dimensions or the native tissue at the delivery site.

13. The method of claim 11, wherein the biological tissue component of the composite graft is similar to the native tissue at the delivery site.

14. The composite graft of claim 1, wherein the biological tissue component is the deceased donor tissue that has been pulverized or morselized.

15. The composite graft of claim 1, wherein the composite graft is further formed by:
    adding a soluble component to the composite mixture, and
    removing the soluble component from the composite graft thereby creating voids in the composite graft, the removing comprising disposing the composite graft in a solution into which the soluble component will dissolve for a period of time sufficient to dissolve the soluble component.

16. The composite graft of claim 1, wherein the composite mixture is uniform.

17. The composite graft of claim 5, wherein the composite mixture comprises the at least one added protein, added cell, pharmaceutical agent, hydration-aiding compound, or combination thereof.

* * * * *